United States Patent [19]

Camp et al.

[11] Patent Number: 4,972,730
[45] Date of Patent: Nov. 27, 1990

[54] SYSTEM FOR DOSING AND DETERMINING SATURATION PRESSURE IN A VOLUMETRIC SORPTION ANALYZER

[75] Inventors: Ronnie W. Camp, Duluth; William B. Conklin, Lilburn, both of Ga.

[73] Assignee: Micromeritics Instrument Corporation, Norcross, Ga.

[21] Appl. No.: 324,152

[22] Filed: Mar. 16, 1989

[51] Int. Cl.$^5$ .......................................... G01N 15/08
[52] U.S. Cl. ................................................... 73/865.5
[58] Field of Search ................................. 73/865.5, 38

[56] References Cited

U.S. PATENT DOCUMENTS

| | | | |
|---|---|---|---|
| 2,729,969 | 1/1956 | Innes | 73/38 |
| 2,788,657 | 4/1957 | Innes | 73/38 |
| 2,960,870 | 11/1960 | Nelsen et al. | 73/865.5 |
| 3,211,006 | 10/1965 | Haley | 73/865.5 |
| 3,211,007 | 10/1966 | Atkins | 73/865.5 |
| 3,262,319 | 7/1966 | Orr, Jr. et al. | 73/865.5 |
| 3,464,273 | 9/1969 | Hendrix et al. | 73/865.5 |
| 3,555,912 | 1/1971 | Lowell | 73/865.5 |
| 3,707,870 | 1/1973 | Herve et al. | 73/38 |
| 3,771,367 | 11/1973 | Lowell et al. | 73/865.5 |
| 3,783,697 | 1/1974 | Lowell et al. | 73/865.5 |
| 3,850,040 | 11/1974 | Orr, Jr. et al. | 73/865.5 |
| 3,884,083 | 5/1975 | Lowell | 73/865.5 |
| 4,566,326 | 1/1986 | Lowell | 73/38 |
| 4,762,010 | 9/1988 | Borghard et al. | 73/865.5 |

FOREIGN PATENT DOCUMENTS

| | | |
|---|---|---|
| 1165432 | 10/1969 | United Kingdom . |
| 1349738 | 4/1974 | United Kingdom ............... 73/865.5 |
| 1449957 | 9/1976 | United Kingdom . |

OTHER PUBLICATIONS

Daeschner, H. W. et al., *An Effective Dynamic Method for Surface Area Determinations*, In Anal. Chem., vol. 34, No. 9, pp. 1150–1155, Aug. 1962.

A Dynamic Nitrogen Adsorption Method for Surface Area Measurements of Paper (by Stone and Nickerson).

Methods and Techniques for the Determination of Specific Surface by Gas Adsorption (by A. S. Joy).

Surface Properties of Porous Solids Low Temperature Nitrogen Adsorption Method (by Shell Method Series 666/49U).

*Primary Examiner*—John Chapman
*Assistant Examiner*—Joseph W. Roskos
*Attorney, Agent, or Firm*—Jones, Askew & Lunsford

[57] ABSTRACT

The invention provides improvements in a system for carrying out volumetric sorption analysis of porous materials. According to one aspect of the invention, the saturation pressure of the adsorbate gas is measured after dosing of the sample during an actual run has brought the adsorbate gas to a saturation condition above the sample, and this measured saturation pressure is then used by the system to determine the relative pressures at which data will be taken during desorption. In accordance with another aspect of the invention, the system automatically adds extra adsorbate gas to the dosing manifold until the analysis proceeds beyond a selected relative pressure, so that far fewer doses are required to reach initial target relative pressures in the case of materials which adsorb large amounts of gas at low relative pressures.

10 Claims, 5 Drawing Sheets

Fig. 1

Fig_2A

Fig_3A

Fig_3B

SYSTEM FOR DOSING AND DETERMINING SATURATION PRESSURE IN A VOLUMETRIC SORPTION ANALYZER

TECHNICAL FIELD

The present invention relates to techniques for determining surface area and pore volume of samples using volumetric adsorption and desorption of gases, and more particularly relates to an improved apparatus and method for determining the saturation pressure of the adsorbed gas and for efficiently dosing samples which adsorb large quantities of gas at low relative pressures.

BACKGROUND ART

The volumetric adsorption method of measuring the pore volume and surface area of porous samples has gained wide acceptance in industry. Instruments for carrying out such analyses are described, for example, in U.S. Pat. No. 3,850,040; and in U.S. Pat. No. 4,566,326. In advanced instruments, each sample is dosed with amounts of an adsorbate gas, such as nitrogen, in order to determine how much of the gas is adsorbed on the surface of the pores of the sample at selected relative pressures $P/P_o$, that is, at certain values of pressure P within the sample chamber relative to the saturation pressure $P_o$ of the gas at the temperature of the sample. The sample is usually maintained at the temperature of liquid nitrogen. Computer controllers have been developed in order to control the dosing of the sample from a manifold to bring the sample pressure up to each target pressure without overshooting it. Control algorithms of this type are described in both of the patents referenced above.

In order to know when target pressures have been reached, the system must be provided with a value for the saturation pressure of the adsorbate gas. Several techniques for determining the saturation pressure $P_o$ have been utilized. In the simplest, $P_o$ is assumed to be equal to atmospheric pressure plus 5–15 Torr. This may be sufficiently accurate for single point BET methods in which the saturation pressure value does not strongly influence the result. However, other measurements, such as obtaining a desorption isotherm for accurate determination of pore volume, require an accurate value for $P_o$, which is very dependent upon temperature.

$P_o$ has also been measured in a different liquid nitrogen ($LN_2$) bath than that in which the sample chamber is immersed. This technique has been utilized in a commercial instrument of the type described in U.S. Pat. No. 4,566,326, by devoting one of the sample stations to an empty cell immersed in its own $LN_2$ bath. The empty cell is filled with nitrogen gas which is liquified, and the vapor pressure is monitored and used as $P_o$. However, the use of a different $LN_2$ bath from that in which the sample is immersed leads to significant errors in the $P_o$ value because of variations in the temperature of the baths.

Another technique is described in U.S. Pat. No. 3,850,040. A separate $P_o$ tube, containing a quantity of suitable material having a large surface area and an amount of adsorbate gas sufficient to condense the gas on the exterior of the material, is immersed with the sample tube into the same $LN_2$ bath. This technique avoids the problem arising from the use of different baths that may vary in temperature, but does not take into account the effect of the sample itself on $P_o$, and therefore is not as accurate as the technique of the present invention, described below.

Finally, $P_o$ has been measured in a different manner a flowing gas adsorption system as described in U.S. Pat. No. 3,555,912. The pressure gauge that is used to indicate the pressure over the sample due to down stream impedance is also used to measure the equilibration vapor pressure $P_o$ of the adsorbate. The entire system is purged with adsorbate, the sample cell is immersed in $LN_2$, and pressure is allowed to build up in the system in order to liquify the adsorbate in the sample cell. The sample cell is isolated, and valves opened to cause the liquid adsorbate to boil, whereby the vapor will flow through the gauge to purge it. Then the purging valve associated with the gauge is closed and the gauge reading taken as $P_o$. By its nature, this technique lacks control over the temperature at which the $P_o$ value is acquired. The flowing adsorbate gas entering the measurement area brings in heat and therefore requires an elevated pressure to liquify, while the vigorous boiling which causes the flow of gas to the gauge can lead to temperature variations caused by uncontrolled cooling. There is no control of the amount of liquid that forms, and the amount may be such that its temperature is different from the temperature of $LN_2$ in the bath. When the flow of gas is reestablished for analysis of the sample, the temperature will vary from that at the time $P_o$ is measured. As a result of these variable factors, this system provides an unreliable measurement of $P_o$.

Thus, it will be seen that there has been a need for a technique and apparatus for obtaining accurate $P_o$ values representing the saturation pressure under conditions essentially identical to those present as the sample is receiving doses of the adsorbate gas during analysis.

Another problem encountered during volumetric sorption analysis is specific to porous materials which adsorb large volumes of adsorbate gas at low relative pressures. This characteristic is typical of materials such as Zeolites and other Type 1 materials, although some Type 2 and Type 4 materials also exhibit large uptake of gas upon initial exposure to the gas. Operators of manual sorption analyzers had the opportunity to guess based upon experience that a particular material might be able to adsorb a large dose of gas without exceeding the first target relative pressure. However, automatic instruments prior to this invention have been incapable of differentiating between relative pressures at which adsorption is large, versus those at which little adsorption occurs. Typically, such instruments have calculated the size of all doses to bring the sample pressure up to the target relative pressure by calculating the gas needed to fill the free space around the sample at the target relative pressure, plus an allowance for adsorption by the sample. This allowance for adsorption must be limited, however, so as not to overshoot the target relative pressures in regions where little additional adsorption occurs. The system described in U.S. Pat. No. 3,850,040 allows the user to elect to increase the size of the dosing manifold by a fixed additional volume, but this would then apply to all doses, not just those at relative pressures at which large adsorption by the sample occurs.

As a result, given a sample that adsorbs large quantities of gas at low relative pressures, over one hundred small doses must sometimes be made by the automatic instrument in order to reach the initial target relative pressures. This repetitive and unproductive procedure wastes time and causes great wear on valves, seals and other components of the gas containing hardware.

Thus, there has been a need for an apparatus and method for controlling dosing in volumetric sorption analyzers capable of avoiding the need for an excessive number of doses in the analysis of Type 1 and similar materials.

SUMMARY OF THE INVENTION

The present invention solves the problems in the art described above by providing improvements in a system for carrying out volumetric sorption analysis of porous materials. According to one aspect of the invention, the saturation pressure of the adsorbate gas is measured after dosing of the sample during an actual run has brought the adsorbate gas to a saturation condition above the sample, and this measured saturation pressure is then used by the system to determine the relative pressures at which data will be taken during desorption. In accordance with another aspect of the invention, the system automatically adds extra adsorbate gas to the dosing manifold until the analysis proceeds beyond a selected relative pressure, so that far fewer doses are required to reach initial target relative pressures in the case of materials which adsorb large amounts of gas at low relative pressures.

Generally described, the invention provides an apparatus and method for measuring the saturation measure of an adsorbate gas by adding an amount of adsorbate gas sufficient to condense the gas on the sample exterior, that is, exterior to the pores of the sample, measuring the saturation pressure of the gas within the sample chamber while the gas is condensed on the sample exterior, and calculating relative pressures based on the measured saturation pressure. Thus, as data is obtained for the adsorption branch of an isotherm, a predetermined saturation pressure is used to determine relative pressures. This predetermined relative pressure may be determined by any of the prior methods described above. The saturation pressure is then measured directly over the sample during the analysis, and the measured $P_o$ is then used to determine relative pressures during the collection of data for the critical desorption branch. Thus, the saturation pressure is obtained taking into account the presence of the sample, and under the same conditions as are experienced by the gas during the remainder of the dosing sequence. A highly accurate saturation pressure is obtained.

The second aspect of the invention may be generally described as an apparatus and method for dosing a sample undergoing volumetric pore volume or surface area analysis, by placing in the dosing manifold an amount of adsorbate gas based upon the amount of sample in the sample chamber; when the relative pressure is below a predetermined level, and then admitting the gas into the sample chamber. The predetermined level of relative pressure may be set depending upon the level of the next selected target relative pressure, or it may be set based upon a measurement of the pressure within the sample chamber following a dose. Thus, at low relative pressures, a significant additional amount of gas per unit of sample in the sample chamber can be dosed onto the sample to accommodate an expected large amount of adsorption at low relative pressures. When the relative pressure reaches a level after which adsorption is expected to proceed at more normal rates, the system can return to doses predicting a more normal amount of adsorption. The return to conventional dosing permits the system to approach target relative pressures without overshooting them.

Thus, it is an object of the present invention to provide an improved method and apparatus for obtaining data for analyzing the surface area or pore volume of porous samples.

It is a further object of the present invention to provide an improved apparatus and method for determining the saturation pressure of an adsorbate gas.

It is a further object of the present invention to provide an improved apparatus and method for reducing the number of doses required to reach low relative pressures for samples which adsorb large amounts of gas prior to reaching initial target relative pressures during volumetric analysis.

It is a further object of the present invention to provide an apparatus and method for determining the saturation pressure of an adsorbate gas in a manner which takes into account the presence of the sample and eliminates differences in temperature between the environment of the sample run and the environment in which the saturation pressure is measured.

It is a further object of the present invention to provide an apparatus and method for dosing a porous sample during volumetric analysis which is flexible enough to provide large doses of adsorbate gas at low relative pressures when appropriate, but also provides more sensitive dosing of the sample at higher relative pressures, in order to obtain data at desired target relative pressures.

Other objects, features and advantages of the present invention will become apparent upon a review of the following detailed description of preferred embodiments, when taken in conjunction with the drawing and the appended claims.

DETAILED DESCTIPTION

Figure 1:
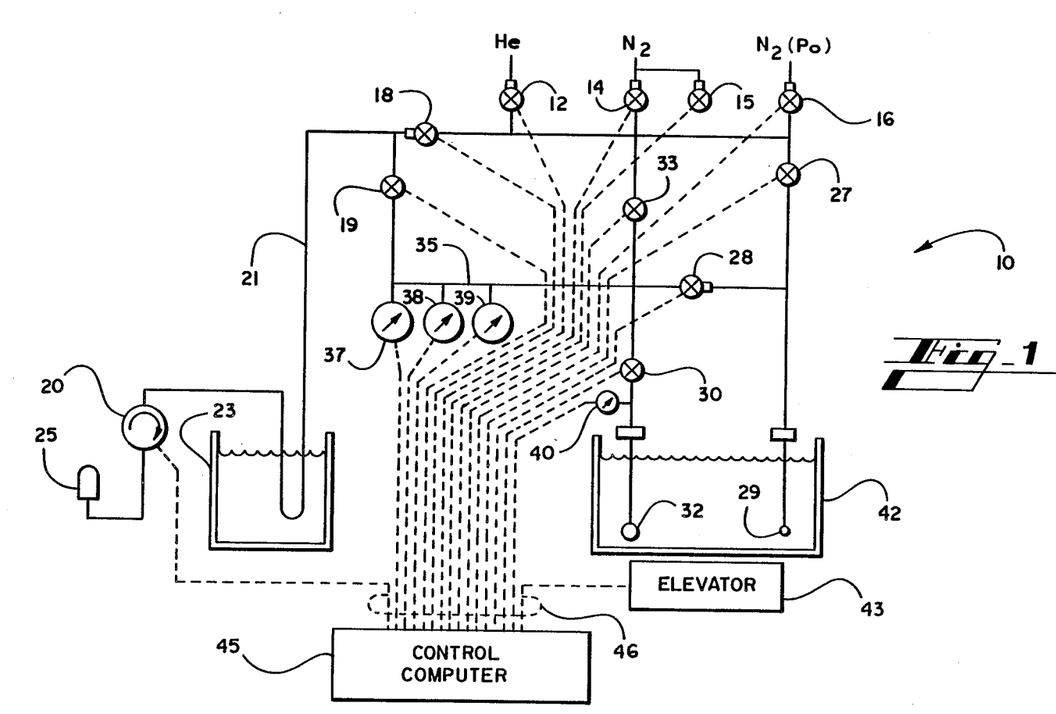
FIG. 1 is a schematic representation of an apparatus embodying the present invention, showing the gas passageways and control signal connections.

Referring now in more detail to the drawing, in which like numerals refer to like parts throughout the several views, FIG. 1 shows a gas flow control apparatus 10 embodying the present invention. Those skilled in the art will understand that a volumetric sorption analyzer may include an environmental control system, a sample preparation system, and other components of the type described in U.S. Pat. No. 3,850,040, which is incorporated herein by reference in its entirety. The present invention relates to improvements in the sample analysis portion of a volumetric sorption analyzer, and the description contained herein will be limited to the portions of the apparatus directly involved in the improvements to sample dosing.

The gas flow control system 10 includes a plurality of restricted flow valves 12, 14, 15 and 16 for admitting gases into the apparatus 10 from storage containers. The valve 12 admits helium gas, which is utilized in initializing the system in a manner described in U.S. Pat. No. 3,850,040. Valve 14 admits nitrogen into the system at a low rate, such as three Torr per second. Valve 15 admits nitrogen from the same source, but at a faster rate, such as 30 Torr per second. Valve 16 admits nitrogen gas from a special source used in connection with the system's conventional capability for determining saturation pressure ($P_o$). A normal flow valve 19 and a restricted flow valve 18 are connected in parallel to form an interface between the system and a vacuum pump 20, which pumps gas through a line 21 through a cold trap loop immersed in a cold trap dewar 23 containing liquid nitrogen. The effluent of the pump 20 passes through a conventional oil mist exhaust filter 25 to atmosphere. A normal flow valve 27 and a restricted flow valve 28 are connected in parallel to interface the system with a conventional $P_o$ tube 29. The $P_o$ tube 29 operates as described above referring to U.S. Pat. No. 3,850,040.

A valve 30 separates a sample tube or chamber 32 from the remainder of the system. It may be seen that a dosing manifold 35 is defined by the fixed volume between the valves 19, 28, 30 and 33. Communicating with the manifold 35 are a plurality of pressure measuring devices 37, 38 and 39. The gauge 37 is a 100 micron vacuum gauge. The device 38 is a ten Torr pressure pressure transducer, preferably having a resolution of 10.5 microns or better. The device 39 is a 1000 Torr pressure transducer preferably having a resolution of 0.05 Torr or better. The pressure measuring devices 37, 38 and 39 are used to measure the pressure within the manifold 35, and within the combined volume of the manifold 35 the sample chamber 32 when the sample valve 30 is open, and within the $P_o$ tube 29 when valve 28 is open. A pressure gauge 40 is located on the sample tube side of the sample valve 30, and measures the pressure in the sample tube when the valve 30 is closed. The device 40 is a 1000 Torr transducer having a resolution of 50 microns or better.

The sample tube 32 and the $P_o$ tube 29 may be selectively immersed in the same bath of liquid nitrogen contained in a Dewar 42. The Dewar 42 may be raised or lowered to immerse or expose the sample tube 32 and $P_o$ tube 29 by means of an elevator 43, in a conventional manner.

Operation and monitoring of the valves, sensors and pump are controlled by a computer processor 45, which may be a programmed general purpose computer. Microprocessors of the type contained in readily available personal computers are capable of operating the apparatus 10. It is within the skill of a programmer of ordinary skill in the art to prepare computer programs to carry out the routines for operating the system described below and depicted in FIGS. 2 and 3, after being provided with the present disclosure. The control computer 45 is connected to the various components of the system by conventional signal transmission lines designated generally as 46. Signals may be transmitted to and from the computer 45 along the lines 46, as appropriate.

Operation of the apparatus 10 will now be described in connection with the flow diagrams shown in FIG. 2 and FIG. 3. It will be understood by those skilled in the art that the present invention can be utilized in connection with a single-sample analyzer of the type shown in FIG. 1, or in connection with a multiple-sample analyzer of the type which utilizes a common manifold and time sharing of control functions to simultaneously analyze several samples in separate sample tubes.

Figure 2A:
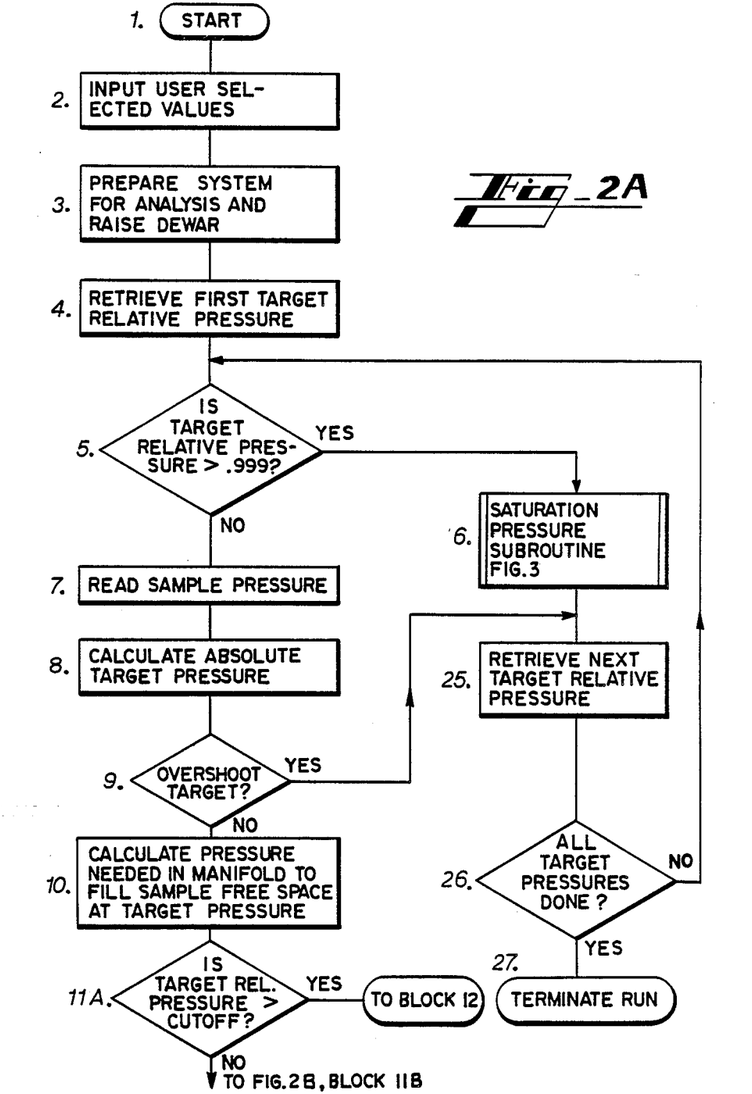
FIGS. 2a and 2b are a logic flow diagram for the dosing routine utilized according to the present invention.
Figure 2B:
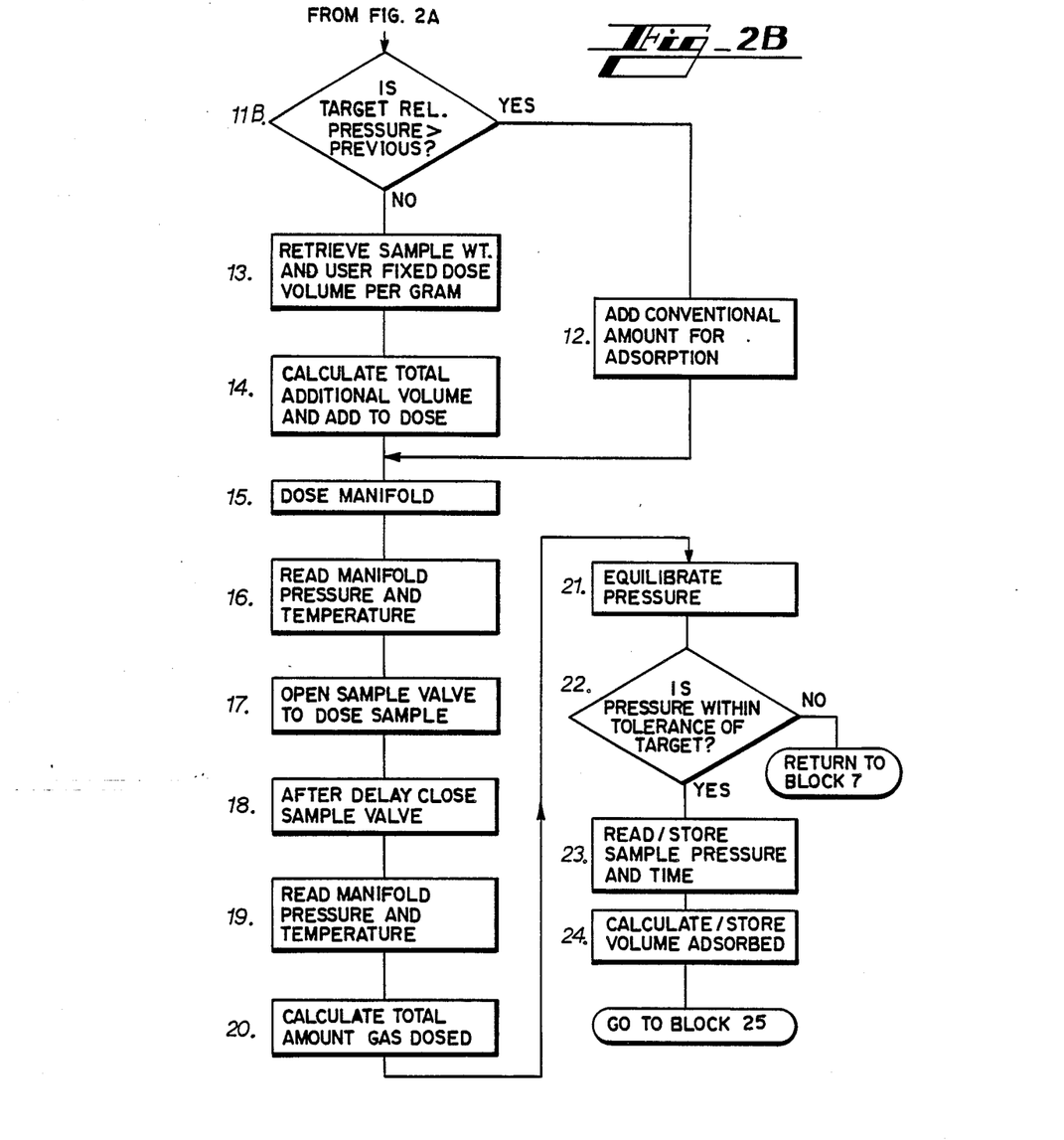

Referring to FIG. 2, prior to the actual analysis user must input several parameters to be used by the control computer during the run. These include a table of target relative pressures at which the user desires to obtain adsorption information to be used in preparing adsorption and/or desorption isotherms. For a purpose to be explained later, the target relative pressures fall between 0 and 1.0, as they represent the ratio $P/P_o$, but any specified relative pressure higher than 0.995 must be 1.0, and triggers the measurement of saturation pressure according to the invention. The user must also specify the equilibration interval used after a dose has been communicated with the sample, and a tolerance within which the pressure in the sample tube must approach the calculated target in order to obtain data at a target relative pressure. For example, the equilibration interval might be specified as five seconds, and the equilibration pressure tolerance 5 percent or 5.0 Torr, whichever occurs first. A separate equilibration time may be set for use as the sample pressure approaches saturation pressure, such as 300 seconds. The purpose of this longer equilibration time is to avoid a false determination of equilibration at high relative pressures. Some samples adsorb gas into the pores of the sample slowly at high relative pressures, which can result in condensation of the gas on the exterior surface, followed by regasification and adsorption of the condensed gas. Extending the period within which equilibration is allowed to occur assures that an interim condensation condition is not interpreted by the control computer as true equilibration.

The user must also enter a cutoff relative pressure, below which an additional amount of gas based on the weight of the sample will be added to each dose during adsorption. The user must determine how much volume of gas per unit weight of sample should be added, and enter this value along with the sample weight. As an example, for a Zeolitic material, the cutoff relative pressure might be selected to be 0.005, and the fixed additional dose 10 cc per gram.

It will also be understood that conventional sample preparation procedures must be carried out before the sample is ready for the sample analysis procedure described in FIG. 2. One procedure for preparing the sample and initializing the system is described in U.S. Pat. No. 3,850,040. Sample materials are degassed before the sample cell is connected to the apparatus 10, the gauges are zeroed, the manifold and sample cell are evacuated, and the Dewar 42 raised by the elevator 43 to immerse the sample tube 32.

The analysis begins at block 4 of FIG. 2, with the retrieval from the computer memory of the first target relative pressure. In block 5, the target pressure is tested to determine whether it is above 0.999, that is, whether it is 1.0. If so, the saturation pressure subroutine of FIG. 3 is carried out. At the beginning of the run, the answer to this inquiry will be no, and the control computer reads the sample pressure as indicated by the gauges 37–39, with the valves 12, 14, 15, 16, 18, 19, 27 and 28 closed, and the valves 30 and 33 open. The absolute pressure needed in the sample chamber to reach the target relative pressures is calculated, and compared to the actual sample pressure. If the pressure has not overshot the target pressure, the control computer calculates the pressure needed in the manifold 35 to fill the free space in the sample cell at the target pressure.

In block 11A of FIG. 2, the target relative pressure as compared to the user entered cutoff relative pressure, below which a fixed additional volume will be added to the dose. If the target relative pressure is above the cutoff, the calculated desired manifold pressure is raised in a conventional manner, for example, by a percentage of the free space, (see U.S. Pat. No. 4,566,326) or by an amount based on predicting the amount that will be adsorbed. The type of conventional dosing technique used is not part of the present invention, which can be used in connection with any dosing system. If the target relative pressure is below the cutoff, and the analysis is in the adsorption branch as determined in block 11B, the control computer retrieves the sample weight and fixed dose volume per gram previously entered by the user. The fixed dose per gram is multiplied by the weight to determine the increase in the desired manifold pressure.

The program as shown assumes that the material being analyzed is a Type 1 material or other material which adsorbs large amounts of gas at low relative pressures. The addition of the fixed dose per weight of sample greatly reduces the number of doses required to reach low target relative pressure. Use of this feature of the invention may be made optional.

Then, in block 15, valve 14 or valve 15 is opened, depending on the volume required, to admit nitrogen from a storage tank into the manifold 35. When the manifold pressure reaches the calculated desired value, the valve 33 is closed to create the accurately known manifold volume, which is now at the calculated pressure at a known temperature. After a delay of about two seconds, the manifold temperature and pressure are measured and stored. Then the sample valve 30 is opened to allow gas from the manifold 35 to mix with that in the sample cell 32. After a delay of 30 seconds, the sample valve is closed. After another two seconds, the manifold temperature and pressure are again read, and, in block 20, the control computer calculates the total amount of adsorbate gas that was transferred from the manifold into the sample cell. The computer also maintains a running total of the cumulative gas dosed from the manifold into the sample cell.

A logical routine is then initiated to determine when adsorption by the sample stops and equilibration is reached within the sample cell, as measured by the gauge 40. The routine is preferably of the type described in U.S. Pat. No. 3,850,040, which uses repetitive pressure measurements to determine when the rate of pressure change within the sample cell has reached a desired minimum level. The resulting equilibration pressure is compared with the target pressure in block 22. If the equilibration pressure is not within the user specified tolerance of the target pressure, the program returns to block 7 to calculate another dose of gas to bring the pressure up to the target pressure. If the pressure is within the specified tolerance, the program moves on to block 23, and stores the pressure in the sample cell as a data point. The computer also calculates the total volume of gas adsorbed by the sample through the preceding dose. Then the next target pressure specified by user is retrieved from the computer memory. If all the target relative pressures listed by the user have not been used, the program returns to block 5, and tests the new target relative pressure to determine whether it is 1.0. If it is not, the program repeats the steps just described to determine adsorption data for target relative pressures along the adsorption isotherm.

It should be noted that pressure calculations to obtain data at target relative pressures along the adsorption isotherm are calculated based upon a saturation pressure $P_o$ of the adsorbate gas determined in the $P_o$ tube 29 in a conventional manner. The $P_o$ tube 29 may be precharged as part of the initialization procedure, as described in U.S. Pat. No. 3,850,040. With all valves closed except valves 27 and 28, the valve 16 can be opened to admit nitrogen into the $P_o$ tube 29 until a high pressure, such as 850 Torr, is present, as measured by the pressure gauges 37-39. Condensation of nitrogen gas within the $P_o$ tube 29 immersed in the $LN_2$ bath 42 provides a measure of the saturation pressure of the adsorbate gas at the temperature of the bath.

In providing the table of target relative pressures, the user may select to determine saturation pressure within the sample cell in accordance with the invention by specifying a target relative pressure of 1.0. When this target relative pressure is reached during the analysis as described in FIG. 2, the computer carries out the saturation pressure routine shown in FIG. 3, in order to determine a new, measured $P_0$ to replace the previously determined saturation pressure obtained using the $P_0$ tube 29. Turning to FIG. 3, if the computer determines that it has not previously obtained a measured $P_0$ in the current run, it tests to determine whether a pair of pressure values $P_1$ and $P_2$ (explained below) have been obtained. At the beginning of the saturation pressure subroutine, this will not be the case, and the program proceeds to block 6 of FIG. 3, and fills the manifold to the maximum system pressure of 925 Torr. It should be understood that this maximum value may vary depending on the sensitivity of the pressure gauges utilized and the nature of the seals, valves and other components of the gas handling apparatus 10. After a delay of two seconds, the pressure in the manifold is measured, and the number of moles of gas in the manifold calculated. Then the sample valve 30 is opened to dose the sample cell with the gas contained in the manifold. After a delay of 30 seconds, the sample valve 30 is closed. Again after a delay of two seconds, the pressure in the manifold is measured, and the remaining moles of gas in the manifold calculated. The difference between $N_2$, the gas remaining in the manifold, and $N_1$, the original amount of gas in the manifold, is added to the running total of gas dosed onto the sample.

The program again tests at block 12 to determine whether $P_1$ and $P_2$ have been obtained. If not, the equilibration interval is set to a relatively short four seconds, and the equilibration pressure tolerance is set to be 95 percent of the value of $P_0$ supplied using the $P_0$ tube 29. Thus the tolerances are relaxed temporarily at this point in the determination of saturation pressure, so that the initial data can be obtained quickly. Then an equilibration saturation tolerance is established equal to the equilibration pressure tolerance, and the pressure within the sample cell is equilibrated in the same manner as described in connection with block 21 of FIG. 2. If the pressure is within the equilibration saturation tolerance, the longer equilibration time noted above, such as 300 sec., may be required.

The computer tests in block 20 to determine whether the equilibration criteria have been met. If so, the computer tests to determine whether pressure $P_1$ has been obtained, and if not (as in the initial pass through the routine) the current sample cell pressure is accepted as $P_1$ and stored. The program goes to block 32, and if $P_2$ has not been obtained, returns to the start of FIG. 3. to provide another dose of gas to the sample cell. If, in block 20, the equilibration criteria have not been met, the program returns to the start of FIG. 3 to dose the sample cell again.

Figure 3A:
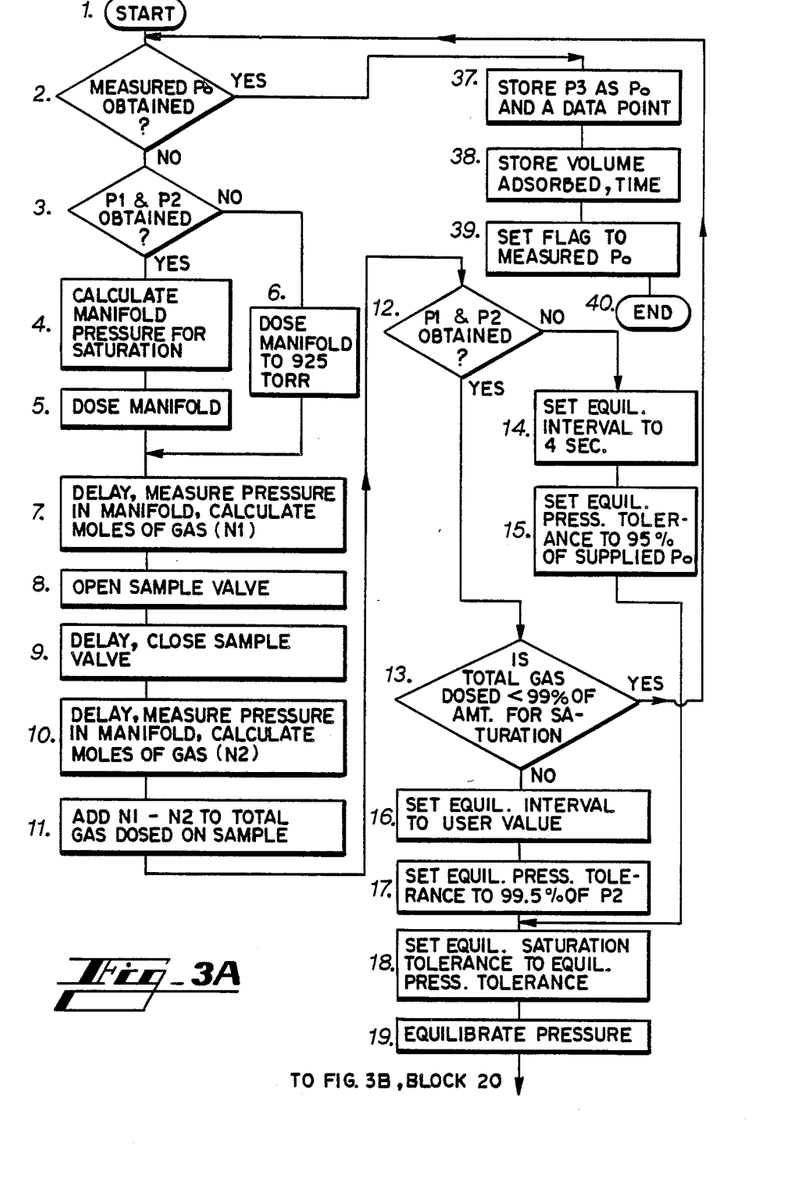
FIGS. 3a and 3b are a logic flow diagram of the routine for determining saturation pressure utilized in connection with the present invention.
Figure 3B:
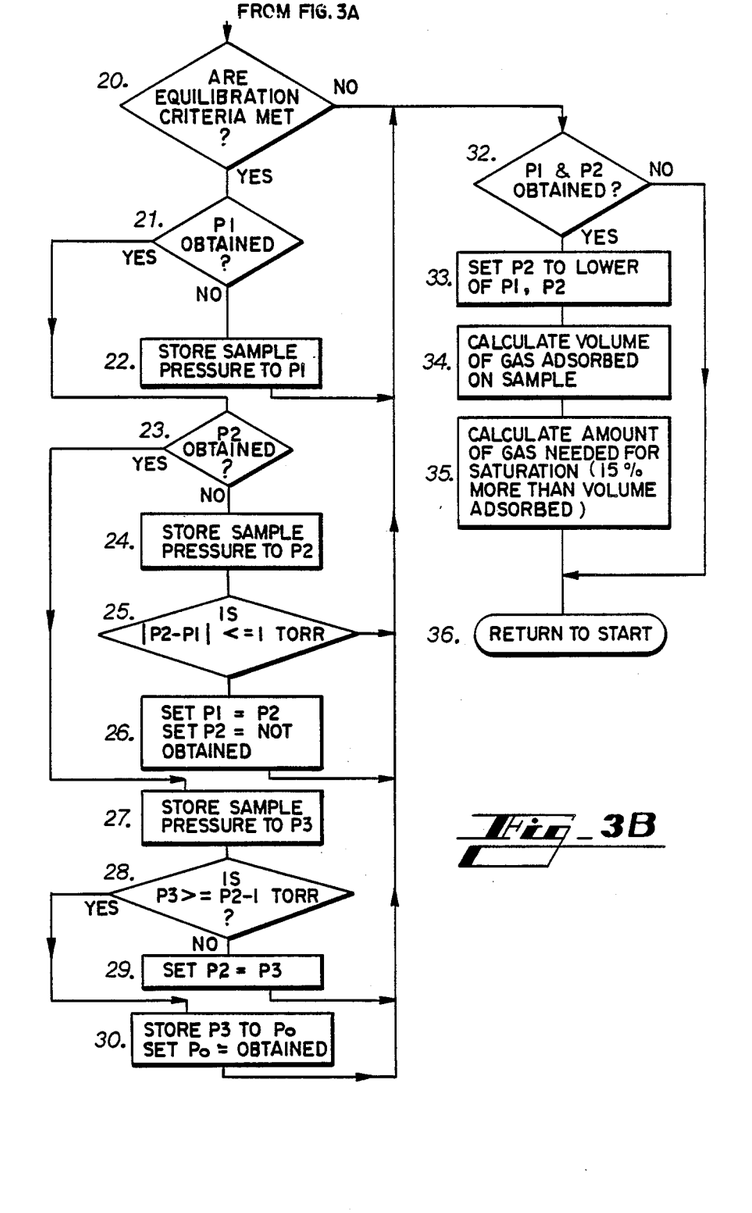

Assuming $P_1$ has been obtained but not $P_2$, the computer, in block 6, again gives the manifold a maximum dose of gas, and repeats the procedures of blocks 7-11 of FIG. 3. Since $P_2$ has not been obtained, the program moves from block 12 to block 14, and the pressure in the sample cell is equilibrated. If the equilibration criteria are met, the program moves from block 20 to block 21. Since $P_1$ was previously obtained, the program jumps to block 23, and then to block 24 since $P_2$ has not been obtained. The current sample cell pressure is accepted and stored as pressure $P_2$. Then, $P_2$ and $P_1$ are compared to determine whether they are within one Torr. If not, $P_1$ is arbitrarily given the value of $P_2$, and the status of $P_2$ is set as not obtained. The program goes to block 32, and since $P_2$ has not been obtained, it goes back to the start of FIG. 3 to dose the sample cell again and try another value of $P_2$.

This is repeated until $P_2$ and $P_1$ are within one Torr. At this point, the program provides a positive response to the inquiry of block 32. At block 33, the value of $P_2$ is set to be the lower of $P_1$ and $P_2$, since only one of these values is needed for the subsequent calculations. Then the computer calculates the total volume of gas adsorbed by the sample. In block 35, the computer calculates an amount of gas that is 15 percent more than the volume thus far adsorbed, and assumes that this is the amount of gas needed for saturation, that is, for condensation of gas on the exterior surface of the sample, exterior to the pores of the sample.

The program then returns to the start of FIG. 3 and indicates that $P_1$ and $P_2$ have been obtained in response to the test of block 3. Moving to block 4, the computer calculates the pressure required in the manifold to provide the amount of gas (from block 35) needed for saturation to the sample cell. This may be more than the maximum dosing pressure for the manifold, in which case the maximum pressure is placed in the manifold. The steps of block 7-11 are repeated to dose the sample again and determine how much gas has been dosed onto the sample. Since, in block 12, $P_1$ and $P_2$ have been obtained, the test for block 13 is carried out to determine whether the total gas dosed onto the sample is less than 99 percent of the calculated amount needed for saturation. If the answer is yes, the program returns to the start of FIG. 3 to provide another dose to the sample. Once the answer to the test of block 13 is no, indicating that the total gas dosed on the sample is within one percent of the amount needed for saturation, the equilibration interval is reset to the user entered value and the equilibration pressure tolerance is tightened to be 99.5 percent of the value of $P_2$. The equilibration saturation tolerance is reset to this same value in block 18, and the pressure in the sample cell is equilibrated. It should be noted that the program does not spend time equilibrating the sample cell pressure until the test of block 13 indicates that the amount of gas needed for saturation has been dosed onto the sample. However, the pressure must equilibrate within 0.5% of $P_2$ to meet the equilibration criteria as tested in block 20. Otherwise, it is assumed that more gas is needed to assure saturation.

Assuming that the equilibration criteria are met, the test of blocks 21 and 23 cause the program to go to block 27, where the current sample cell pressure is accepted as $P_3$. This value is then tested to determine whether it is no less than one Torr below $P_2$. If so, $P_3$ is accepted as the measured $P_0$, and the status of $P_0$ is set to obtained. The program follows its normal course to block 34, at which the volume of gas adsorbed on the sample is calculated. Then when the program returns to the start of FIG. 3, the test in block 2 of whether a measured $P_0$ has been obtained obtains an answer of yes, and the value of $P_3$ is stored both as measured $P_0$ and as a data point. The volume adsorbed is stored, along with the time the data point was taken, and a flag in the memory is set to indicate that the measured $P_0$ should be used in place of the supplied $P_0$ from the $P_0$ tube 29, in calculations relating to target relative pressures during the desorption portion of the analysis.

Returning to block 29, when $P_3$ is lower than one Torr below $P_2$, the value of the $P_2$ is set to be the value of $P_3$. Moving to block 29 would be an uncommon occurrence, possibly happening when the 4 second interval at block 14 is too short for the particular material. The program moves to a recalculation in block 35, and the addition of another 15 percent of the gas previously adsorbed to the calculated amount needed for saturation. The lowering of the value of $P_2$ also relaxes the test for saturation to a lower pressure. This may be repeated until, in block 28, $P_3$ is high enough compared to $P_2$, at which time it is acceptable to serve as $P_0$.

Thus, the saturation pressure is determined in the sample tube under the conditions of analysis over the sample. The unique algorithm described above is used to determine when saturation has occured. When $P_2$ and $P_1$ become essentially the same, this indicates that the addition of significant amounts of gas to the sample cell have not resulted in any rise in pressure, an indication that all new gas introduced into the sample cell is condensing. An additional 15 percent of the amount adsorbed is added to assure that saturation has occured.

The following table shows a comparison of $P_0$ values obtained using prior art methods with the more accurate $P_0$ value obtained using the saturation pressure routine just described. The measurements of the saturation pressure of nitrogen were taken on the same ASAP 2400 Analyzer at the same time, using freshly drawn $LN_2$ in the baths. The current atmospheric pressure is given as a reference point. The differences shown would exert a noticeable effect on sorption results.

TABLE 1

| NITROGEN SATURATION PRESSURE COMPARISON | |
| --- | --- |
| Method | $P_o$ |
| 1. Atmospheric Pressure | 729.85 |
| 2. Atmospheric Pressure Plus 15 Torr | 744.85 |
| 3. $P_o$ Tube in Separate $LN_2$ Bath | 735.39 |
| 4. $P_o$ Tube in Same Bath with Sample | 736.01 |
| 5. Measured Over Sample In Sample Tube During Analysis Per Invention | 736.53 |

At the end of the saturation pressure subroutine of FIG. 3, the computer returns to block 25 of the sample analysis routine of FIG. 2. Since the last target relative pressure was 1.0, the next target relative pressure will be a lower relative pressure, on the desorption branch of the isotherm. The measured $P_o$ value is very accurate, and therefore assures that the hysteresis portion of the desorption isotherm will be accurate and reproducible. When the first relative pressure on the desorption isotherm is specified, the pressure in the sample cell 32 is read in block 7 of FIG. 2, and then in block 10 the computer calculates how much gas should be removed from the sample cell to lower the sample pressure to the first target relative pressure on the desorption isotherm. The test of block 11A obtains a positive response, so that the program skips the fixed dose increment feature of blocks 13 and 14. In block 15, the manifold is "dosed" by pulling a partial vacuum sufficient to reduce the sample pressure to the calculated value when the sample valve is opened. However, even when the target relative pressure becomes less than the user specified cutoff value for the fixed dose increment, in block 11B the test of whether the target relative pressure is less than the previous target relative pressure gets a positive response when the analysis is along the desorption branch, and therefore the fixed dose additional volume is never withdrawn from the manifold during desorption.

The program proceeds just as it did in the case of adsorption, dealing with amounts of gas withdrawn from the sample rather than amounts adsorbed. When all the target pressures have been dealt with, the test of block 26 results in termination of the run. Conventional routines are then carried out to warm the sample and carry out data reduction to present the results of the analysis in an easily usable format. During data reduction, the program preferably recalculates all of the data points for the adsorption branch of the isotherm using the new measured $P_o$ value that was obtained during the analysis. Since this measured $P_o$ value is more accurate than the supplied $P_o$ value initially utilized in conducting the adsorption analysis, recalculation allows the presentation of more accurate results for both branches of the isotherm.

It should be noted that the present invention can be utilized in connection with programs which speed up the duration of analysis by multiple-sample simultaneous analyzers. An example of a sophisticated multiple-sample analyzer is the Model ASAP 2400 sorption analyzer manufactured by Micromeritics Instrument Corporation. Such multi-sample systems may operate in either of two modes. In one mode, each sample is degassed and otherwise prepared individually, with the system exercising time sharing routines to utilize the manifold and other common components of the system for each sample in turn, preferably while the other samples are experiencing necessary waiting times or are involved with separate components of the system.

High throughput modes of operation have also been developed, which can more than double the number of samples run per day for some users. This improvement in productivity has been achieved by eliminating the free space measurement by measuring it once for each sample tube and relying on this fixed number for successive runs of the same sample tube; eliminating the saturation pressure measurement for BET surface area analysis and allowing the operator to enter a recently determined value; using batch operations for initial evacuation, back filling and final warming of all the sample tubes together; measuring saturation pressure in accordance with the present invention for desorption pore volumes directly over the sample as part of the saturation process prior to beginning desorption; implementing the dosing procedure according to the present invention to accelerate very low relative pressure point dosing by permitting the operator to specify an excess dose increment operative below a specified relative pressure; and providing a maximum dose routine to quickly saturate samples where no adsorption pore volume distribution data is needed. This mode works best when the user's samples are roughly similar in nature as often is the case in quality control work or in research involving differential treatments on the same base material.

While this invention has been described with particular reference to preferred embodiments thereof, it will be understood that variations and modifications can be made without departing from the scope of the invention as defined in the appended claims.

What is claimed is:

1. In a method of determining saturation pressure of an adsorbate gas and using said saturation pressure in volumetric sorption analysis of a porous sample in a chamber, the improvement comprising the steps of:
   (a) adding an amount of said gas sufficient to condense said gas on said sample exterior to the pores of said sample;
   (b) measuring the saturation pressure of said gas within said chamber while said gas is condensed on said sample exterior to the pores of said sample; and
   (c) calculating relative pressures based on said measured saturation pressure.

2. The method of claim 1, wherein said step of adding an amount of said gas sufficient to condense said gas on said sample exterior to the pores of said sample comprises:
   adding said gas sufficient to raise the pressure within said chamber to a first pressure within a set tolerance of a previously determined saturation pressure;
   adding an additional amount of said gas sufficient to raise the pressure within said chamber to a second pressure within a set tolerance of said previously determined saturation pressure;
   calculating the total volume of said gas adsorbed by said sample; and
   responsive to the difference between said first and second pressures being less than a predetermined value, adding an amount of said gas equal to a selected fraction of said total volume adsorbed.

3. The method of claim 2, wherein said step of adding an amount of said gas equal to a selected fraction of said total volume adsorbed comprises adding fifteen per cent of said total volume adsorbed.

4. In an apparatus for determining saturation pressure of an adsorbate gas and using said saturation pressure during volumetric sorption analysis of a porous sample in a chamber, the improvement comprising
   means for adding an amount of said gas sufficient to condense said gas on said sample exterior to the pores of said sample;
   means for measuring the saturation pressure of said gas within said chamber while said gas is condensed on said sample exterior to the pores of said sample; and
   means for calculating relative pressure based on said measured saturation pressure.

5. The apparatus of claim 4, wherein said means for adding an amount of said gas sufficient to condense said gas on said sample exterior to the pores of said sample comprises means for:
   adding said gas sufficient to raise the pressure within said chamber to a first pressure within a set tolerance of a previously determined saturation pressure;
   adding an additional amount of said gas sufficient to raise the pressure within said chamber to a second pressure within a set tolerance of said previously determined saturation pressure;

calculating the total volume of said gas adsorbed by said sample; and responsive to the difference between said first and second pressures being less than a predetermined value, adding an amount of said gas equal to a selected fraction of said total volume adsorbed.

6. The apparatus of claim 5, wherein said selected fraction of said total volume adsorbed is fifteen per cent.

7. In a method of providing doses of an adsorbate gas to a sample undergoing volumetric sorption analysis in a chamber, the improvement comprising the steps of:

at relative pressures below a predetermined relative pressure, initiating the admission of an additional amount of said gas with each of said doses into said chamber based upon the adsorptive properties of said sample, and the amount of said sample in said chamber; and at relative pressures above said predetermined relative pressure, terminating the admission of said additional amounts of gas.

8. In an apparatus for providing doses of an absorbate gas to a sample undergoing volumetric sorption analysis in a chamber, the improvement comprising:

means for initiating the admission of an additional amount of said gas with each of said doses into a manifold, at relative pressures below a predetermined relative pressure, based upon the adsorptive properties of said sample, and the amount of said sample in said chamber;

means for terminating the admission of said additional amount of gas into said manifold, at relative pressures above said predetermined relative pressure; and valve means for admitting said additional amount of gas from said manifold into said chamber.

9. In a method of providing doses of an adsorbate gas to a sample undergoing volumetric sorption analysis in a chamber, the improvement comprising the step of:

at relative pressures below a predetermined relative pressure, admitting to said chamber an amount of gas based upon the amount of said sample in said chamber such that said amount of gas is equal to a selected volume per weight times the weight of said sample.

10. In an apparatus for providing doses of an adsorbate gas to a sample undergoing volumetric sorption analysis in a chamber, the improvement comprising:

means for adding an amount of said gas to a manifold based upon the amount of said sample in said chamber, comprising means for adding an amount equal to a selected volume per weight times the weight of said sample, at relative pressures below a predetermined relative pressure; and valve means for admitting said gas from said manifold into said chamber.

* * * * *